United States Patent [19]

Sargent

[11] Patent Number: 5,571,956
[45] Date of Patent: Nov. 5, 1996

[54] APPARATUS AND METHOD FOR TESTING THE SHARPNESS OF CUTTING EDGES

[75] Inventor: Lee A. Sargent, Roggen, Colo.

[73] Assignee: Monfort, Inc., Greeley, Colo.

[21] Appl. No.: 310,235

[22] Filed: Sep. 21, 1994

[51] Int. Cl.$^6$ ........................................... G01N 3/58
[52] U.S. Cl. ............................................... 73/104
[58] Field of Search .................................. 73/104

[56] References Cited

U.S. PATENT DOCUMENTS

| | | | |
|---|---|---|---|
| 1,176,291 | 3/1916 | Herbert et al. | 73/104 |
| 1,983,597 | 12/1934 | Casselman . | |
| 2,055,125 | 9/1936 | Floyd . | |
| 2,226,927 | 12/1940 | Hall . | |
| 2,472,994 | 6/1949 | Vars | 73/104 |
| 3,807,225 | 4/1974 | Jepson et al. | 73/104 |
| 3,817,090 | 6/1974 | Michel | 73/81 |
| 3,827,281 | 8/1974 | Hamel | 73/7 |
| 3,869,802 | 3/1975 | Pirner . | |
| 3,902,358 | 9/1975 | Moore | 73/104 |
| 3,931,732 | 1/1976 | von Heitlinger | 73/104 |
| 4,178,797 | 12/1979 | Kozlowski, Jr. | 73/104 |
| 5,196,800 | 3/1993 | Graff et al. | 324/662 |
| 5,379,633 | 1/1995 | Flisram et al. | 73/104 |

*Primary Examiner*—Thomas P. Noland
*Attorney, Agent, or Firm*—Sheridan Ross & McIntosh

[57] ABSTRACT

The present invention relates to an apparatus and method for quantitatively measuring the sharpness of cutting edges. The apparatus includes gripper assemblies for securing a cutting medium that allows for adjustment of a cutting medium to specific angular orientations, a sleeve for holding an edge so that the edge is capable of contacting the cutting medium, an electric actuator for relatively moving the edge relative to the cutting medium and a force strain gauge for quantitatively measuring the sharpness of the edge as the edge relatively moves relative to the cutting medium.

11 Claims, 4 Drawing Sheets

5,571,956

APPARATUS AND METHOD FOR TESTING THE SHARPNESS OF CUTTING EDGES

FIELD OF THE INVENTION

This invention relates to the field of measuring the sharpness of cutting edges, and more particularly, to an apparatus and associated method for quantitatively measuring the sharpness of cutting edges.

BACKGROUND OF THE INVENTION

Various devices have been previously designed to measure the sharpness of cutting edges. For example, U.S. Pat. No. 4,178,797 to Kozlowski discloses a machine for testing the sharpness of knives, particularly surgical knives, where the sharpness of a blade is determined by the number of turns required to cut through a cylindrical spinning rod made of rubber or plastic. U.S. Pat. No. 2,472,994 to Vars discloses a device which tests the sharpness of a knife blade by causing a piece of paper to be drawn downwardly toward the blade and measuring the depth of cut in the paper. U.S. Pat. No. 3,827,281 to Hamel discloses a method and apparatus for testing the abrasiveness of materials, such as paper, by pressing an easily dulled cutting edge through a plurality of paper layers to ascertain the abrasion characteristics of the paper.

These available devices and methods for testing knife blade sharpness are deficient in several respects. For example, to obtain sharpness measurements using the apparatus disclosed in U.S. Pat. No. 4,178,797 to Kozlowski, an operator must count the number of turns of the handle until the knife cuts through the cutting medium. Such sharpness measurements can be imprecise and inaccurate, not to mention unreliable and not easily reproduced. In addition, the apparatus can only measure the sharpness of a single, specific portion of the knife.

The apparatus disclosed in U.S. Pat. No. 2,472,994 to Vars exhibits similar deficiencies in terms of accuracy, precision and reproducibility of sharpness measurements. The Vars apparatus can only measure the depth of cut in a piece of paper drawn over an edge and does not permit quantitative sharpness measurements to be obtained for discrete portions of an edge or along the entire length of an edge. Thus, the Vars apparatus does not permit one to quantitatively determine whether a cutting edge is uniformly of a desired sharpness.

Finally, the invention described in U.S. Pat. No. 3,827,281 to Hamel is designed to test the abrasiveness of materials, such as paper, by measuring depth of cut through the paper and is not designed to measure the sharpness of an edge, especially discrete portions thereof.

None of these available devices and methods for testing knife edge sharpness can quantitatively measure the sharpness of an edge with a high degree of precision, reliability or reproducibility. In addition, none of these devices and associated methods quantitatively measure the sharpness of an edge at discrete segments of or along a substantial or length of the edge.

In view of these deficiencies, a need exists to provide an apparatus and method for testing the sharpness of cutting edges that is capable of producing quantitative, accurate, reliable and reproducible sharpness measurements. Because typical cutting motions utilize not only specific portions of an edge, but also various lengths of an edge, it would also be beneficial to provide an apparatus and associated method for measuring the sharpness of an edge, at consecutive, discrete points on an edge, and/or along the entire length of the edge.

SUMMARY OF THE INVENTION

The present invention is directed to an apparatus and method that can quantitatively measure the sharpness of an edge with a high degree of precision, accuracy, reliability and reproducibility. The present invention allows quantitative sharpness measurements of an edge at discrete segments along the edge, and/or at discrete segments along the entire length of the edge.

Using the present invention, it is possible to determine which portions of an edge require sharpening most often to predict when such edges will require replacement or sharpening. Maintaining sharp edges increases the efficiency of individuals who continuously cut and slice products and reduces the stress and strain involved in performing cutting operations.

The present invention is capable of providing tension or compression to a cutting medium in order to more accurately and reliably measure the sharpness of an edge or to determine the frictional effects of buffing the sides of a knife. The present apparatus is easy to use, maintain, clean and retool.

In one embodiment, the present apparatus includes a means for securing a cutting medium that allows for adjustment of the cutting medium to specific angular orientations, a means for holding an edge so that the edge is capable of contacting the cutting medium, a means for relatively moving the edge relative to the cutting medium, and a means for measuring the sharpness of the edge as the edge relatively moves relative to the cutting medium.

Preferably, the present invention quantitatively measures the sharpness of an edge at discrete segments of an edge, and/or along the entire length of an edge. In order to quantitatively measure the sharpness of an edge at discrete segments along a substantial length of an edge, the present invention includes at least one securing means which can angularly adjust the orientation of the cutting medium. Preferably, an upper and lower securing means hold the cutting medium at a specific angular orientation. Where a substantial length of an edge is to be measured for sharpness, a projection of the cutting medium is provided that is greater than or equal to a projection of the substantial length of the edge.

In another embodiment of the present invention, the apparatus includes a means for tensioning the cutting medium. Providing lateral and/or longitudinal tension to the cutting medium increases the accuracy, reliability and reproducibility of the sharpness measurements. Preferably, tension may be provided to the cutting medium by the securing means.

The apparatus of the present invention also includes a holding means. The holding means secures a cutting edge and allows a cutting edge to contact a cutting medium. In a preferred embodiment, the holding means is capable of allowing angular adjustment of an edge in a plane relatively perpendicular to the cutting medium to simulate various cutting configurations.

A means for relatively moving the edge relative to a cutting medium is provided whereby the edge relatively moves at a substantially constant velocity or, alternatively, under a substantially constant force, relative to the cutting medium. The moving means of the present invention is preferably operatively associated with the holding means with a measuring means interposed therebetween to move the edge through a cutting medium. Alternatively, in another embodiment, the moving means may be operatively associated with the securing means to move the cutting medium relative to an edge. In a preferred embodiment, the moving means includes an electrical or mechanical device, such as a motorized linear actuator, to move an edge through a cutting medium with a substantially constant force or at a substantially constant velocity.

The apparatus of the present invention also includes a measuring means designed to quantitatively measure the force required for an edge, moving at a substantially constant velocity, to relatively move relative to a cutting medium. Alternatively, the measuring means can measure the velocity (or time) at which an edge relatively moves relative to a cutting medium with a substantially constant force. The measuring means preferably provides substantially continuous sharpness measurements along the entire length of an edge and such measurements are correlated with discrete segments of the edge, preferably by a computer.

DETAILED DESCRIPTION

Figure 1:
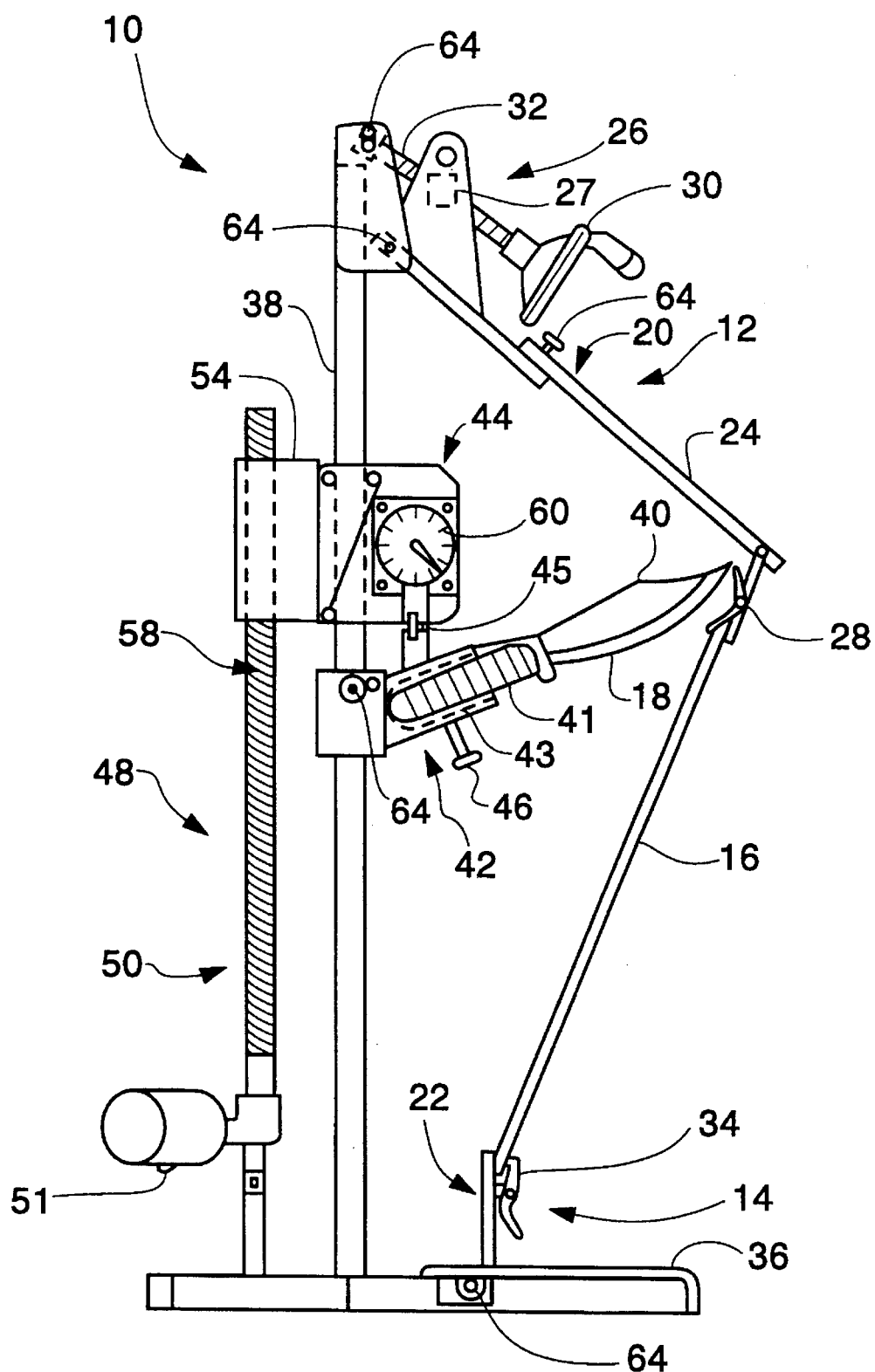
FIG. 1 illustrates a side view of one embodiment of the apparatus of the present invention with a cutting medium mounted thereon.

The present invention relates to the quantitative measurement of the sharpness of various cutting edges, such as knives and other cutting instruments. Such measurements may generally be accomplished in two ways. The sharpness of an edge may be determined by measuring the force required for an edge, moving at a substantially constant rate, to cut through a cutting medium. Alternatively, the sharpness of an edge may be determined by measuring the rate at which an edge, moving with a substantially constant force, cuts or slices through a cutting medium. Using one of these methods, the present invention provides a quantitative measurement of the sharpness of edges.

Generally, the apparatus of the present invention includes a means for securing a cutting medium, a means for holding a cutting edge, a means for relatively moving the cutting edge relative to the cutting medium, and a means for quantitatively measuring the sharpness of the edge, generally indicated by force, velocity or time measurements. In order to provide a durable, dependable, yet inexpensive edge sharpness tester, the securing means, holding means and the moving means can be fabricated from any suitable rigid material, such as metal, wood, plastic or fiberglass. Additionally, the means for quantitatively measuring the sharpness of the edge can be selected from the group consisting of force strain gauges, dynamometers, timers, speedometers, and tachometers. In order to obtain consistent, reliable and reproducible measurements of edge sharpness, the cutting medium should be a material of substantially uniform composition, hardness and/or density, preferably selected from the group consisting of rubber, meat, wood, fabrics, cardboard, paperboard, posterboard, plastic and other synthetic materials.

The securing means of the present invention should be capable of securing a cutting medium in close proximity to the edge to be tested. In this way the edge can contact and efficiently cut or slice through the cutting medium. The holding means generally supports and positions the edge in close proximity to the cutting medium. The present invention also includes a moving means, which relatively moves the edge relative to the cutting medium. In one embodiment of the present invention, the moving means causes the edge to slice through the cutting medium with a substantially constant force or, alternatively, at a substantially constant rate. In another embodiment of the present invention, the moving means moves the cutting medium while the edge remains stationary. The moving means may be operatively associated with the holding means and measuring means, or, alternatively, the securing means. The measuring means may be operatively associated with and interposed between the moving means and the holding means, or, alternatively, operatively associated with the securing means and the cutting medium. Additionally, the securing means, holding means, moving means and/or the measuring means may be operatively associated with a stand, which provides support and stability to the present invention.

Figure 2:
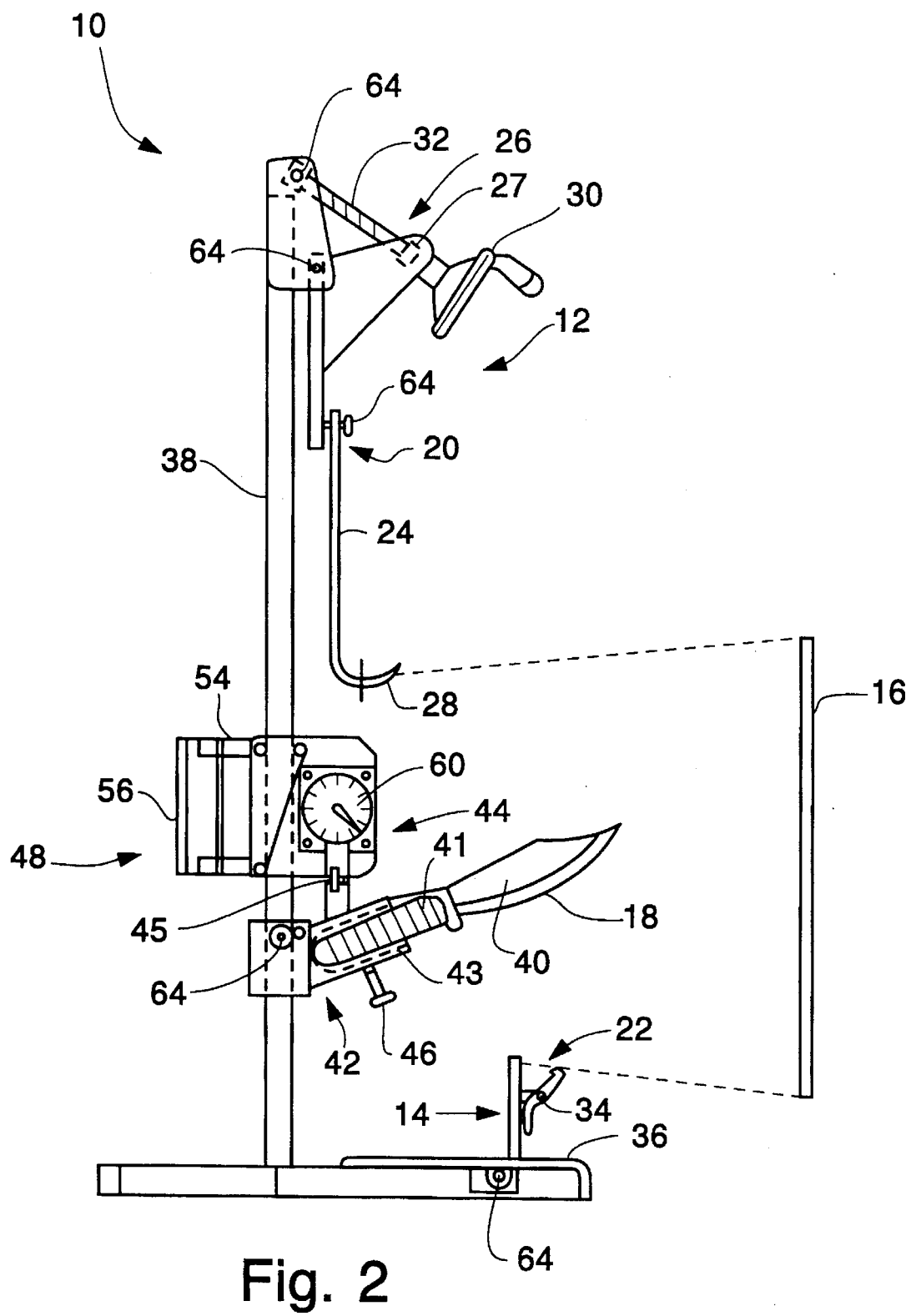
FIG. 2 illustrates an exploded side view of another embodiment of the apparatus of the present invention with a suspended cutting medium.
Figure 3:
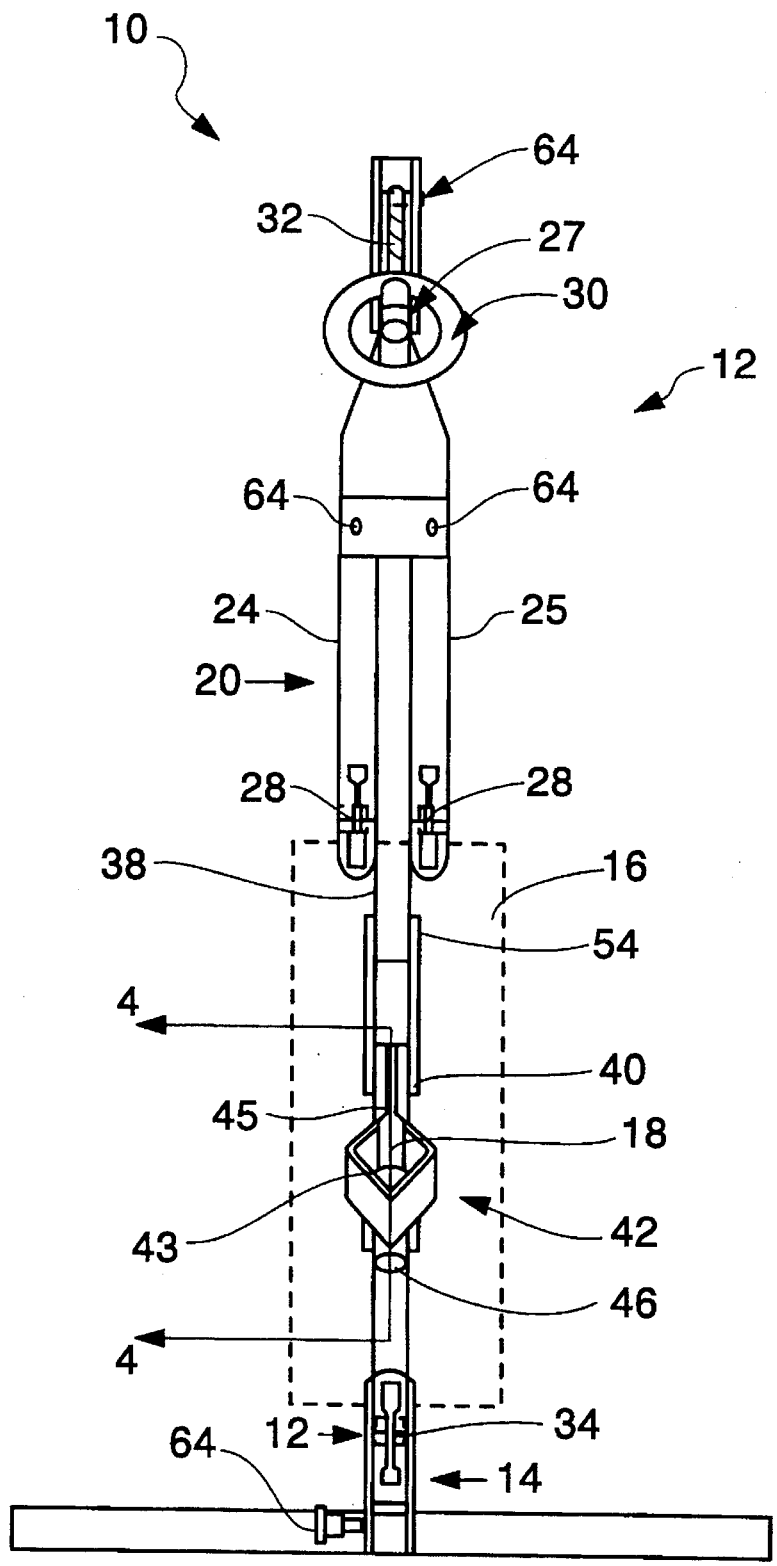
FIG. 3 illustrates a front view of the embodiment shown in FIG. 1 with the cutting medium suspended in front of the apparatus.

The securing means may secure the cutting medium at various positions and orientations. Generally, the apparatus of the present invention includes at least one securing means. Preferably, as shown in FIGS. 1–3, the apparatus 10 includes an upper and a lower securing means 12, 14. An upper securing means 12 may hold or secure an area in the upper portion of the cutting medium 16 while a lower securing means 14 may secure an area in the lower portion of the cutting medium 16, as shown in FIG. 1. The upper and lower securing means 12, 14 are generally capable of adjusting the lateral and/or longitudinal position of the cutting medium 16. In this regard, the angular orientation of the cutting medium 16 may also be readily adjusted. For purposes of clarification and understanding of the present invention, the cutting medium 16 shown in FIGS. 2–3 is not connected to the securing means 12, 14. FIGS. 2–3 therefore illustrate the apparatus 10 and a suspended cutting medium 16.

Figure 4A:
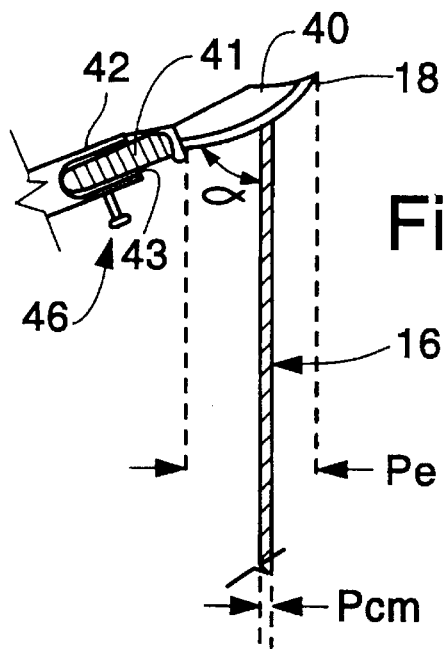
FIG. 4a illustrates a side view of the embodiment of FIG. 3 taken along line 4—4 and shows an angular orientation of the cutting medium and an angular configuration of the edge where a specific portion of the edge is to be measured for sharpness.
Figure 4B:
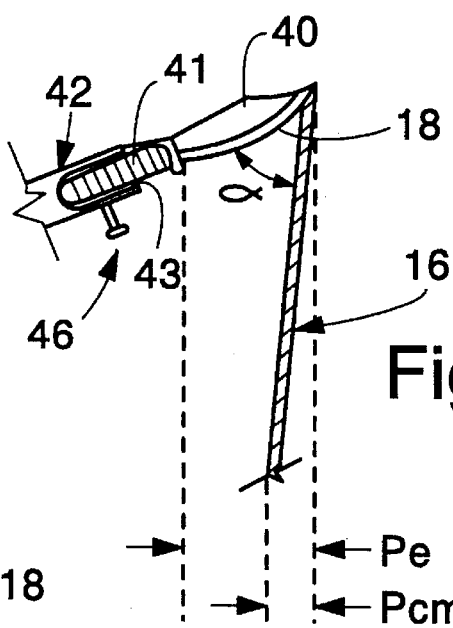
FIG. 4b illustrates a side view of the embodiment of FIG. 3 taken along line 4—4 and shows an angular orientation of the cutting medium and an angular configuration of the edge where segments of an edge are to be measured for sharpness.
Figure 4C:
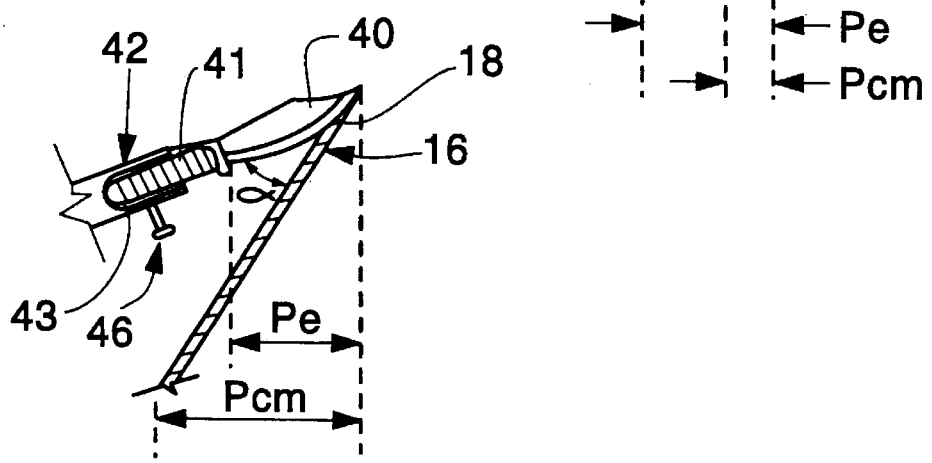
FIG. 4c illustrates a side view of the embodiment of FIG. 3 taken along line 4—4 and shows an angular orientation of the cutting medium and an angular configuration of the edge where segments along the entire length of the edge are to be measured for sharpness.

As illustrated in FIG. 1, adjusting the angular orientation of the cutting medium 16 is especially important in measuring the sharpness of an edge 18 at discrete segments of the edge 18 along a substantial portion or the entire length of the edge 18. In this regard, as shown in FIGS. 4a–4c, in order to quantitatively and efficiently measure the sharpness of discrete segments of the edge 18 along the entire length of the edge 18, the upper and lower securing means 12, 14 may be adjusted to a plurality of angular orientations so that a projection of the cutting medium (Pcm) 16 substantially corresponds to or is greater than a projection of the cutting edge (Pe) 18 as shown in FIG. 4c. The upper and lower securing means 12, 14 are also capable of adjusting the angular orientation of the cutting medium 16 such that the projection of the edge 18 is greater than the projection of the cutting medium 16, as shown in FIGS. 4b–c. In such instances, sharpness of the edge 18 may be measured at a relatively short segment of the edge 18, roughly equivalent in length to the thickness of the cutting medium 16, or, where the projection of cutting medium 16 is extended, as shown in FIG. 4b, sharpness of the edge 18 may be measured along a substantial length of the edge 18. In short, the securing means of the present invention is capable of allowing the cutting medium to be angularly positioned to a number of angular orientations to permit quantitative measurement of the sharpness of the edge at discrete segments along a substantial portion of, or the entire length of, the edge 18. For instance, where the cutting medium 16 is initially oriented parallel to the stand 38, as shown in FIGS. 1–3, the securing means 12, 14 may be capable of allowing angular adjustments of the cutting medium ranging from 0°–90°, in either direction.

In order to securely adjust and maintain the angular orientation of the cutting medium 16, the upper and lower securing means 12, 14 may include arm assemblies 20 and/or gripper assemblies 22. Although FIGS. 1–3 show an upper securing means 12 utilizing an arm assembly 20 and a lower securing means 14 utilizing a gripper assembly 22, it is expressly understood that other means of securing the cutting medium 16 can be employed and that the upper and lower securing means 12, 14 may utilize either the arm assembly 20, gripper assembly 22 or both.

As illustrated in FIGS. 1–3, the arm assembly 20 may generally include at least one arm 24, an arm adjustment mechanism 26, and at least one fastener 28 for holding the cutting medium 16. In order to securely hold the cutting medium 16 so that the cutting medium does not substantially move during the test cutting operation, the arm assembly 20 preferably includes two arms 24, 25. In one embodiment of the present invention, the two arms 24, 25 can be adjusted to move arcuately by the arm adjustment mechanism 26, namely, by rotating an arm adjustment wheel 30 which is operatively associated with a threaded block 27. Preferably, the inner diameter of block 27 is greater than the outer diameter of the threaded rod 32 to facilitate movement of the rod 32. Since the arm adjustment wheel 30 is operatively associated with a threaded rod 32, which, in turn is operatively associated with the arms 24, 25, the rotational movement of the wheel 30 is translated to the arms 24, 25 to move the arms arcuately. Frictional effects between the threaded rod 32 and the block 27 maintain the position of the arms 24, 25 when adjusted such that at least one of the plurality of angular orientations of the cutting medium 16 can be maintained. In the embodiment shown in FIG. 3, the two arms 24, 25 are mounted and attached to each other at a specific angular orientation and distance from each other. Thus, due to the coextensive mounting configuration of the arms 24, 25, it can be appreciated that each arm can be simultaneously adjusted upwardly and outwardly from the stand, along a longitudinally oriented arc. As a consequence of such coextensive mounting, the securing means, namely, an arm adjustment mechanism 26, can adjust the angular orientation of the cutting medium 16 simply by arcuately moving the arms 24, 25 of the arm assembly 20.

In another embodiment (not shown), each arm may be in operative relation to separate arm adjustment assemblies to permit independent movement of each arm. Specifically, each arm may be attached to its own arm adjustment mechanism 26, or more specifically, arm adjustment wheel 30. Alternatively, in another embodiment (not shown), instead of an arm adjustment wheel 30, the arm adjustment mechanism 26 may comprise a device selected from the group consisting of ratchets, chains and sprockets, levered mechanisms, cams, pulley systems or linear actuators, such as a pneumatic, electric or hydraulic pistons or an electric acme ball and screw actuator in order to provide the arms with longitudinally oriented arcuate motion. In such an embodiment, both arms may be in operative relation to the arm adjustment mechanism to permit simultaneous positioning of the arms or, alternatively, each arm may be connected to separate arm adjustment mechanisms to move independently of each other.

The arm assembly 20 should also include fasteners 28 for securing the cutting medium 16 to the arms 24, 25, as shown in FIG. 1. The fasteners 28 may be selected from the group consisting of clamps, latches, lugs, hooks, prongs, u-shaped members, toggles, screws, pins, rivets, cabling, couplings and various other similar fasteners. In preferred embodiments, clamps or toggles are used to secure the cutting medium 16 to the arms 24, 25. The cutting medium 16 should be securely held by the securing means 12, 14 such that the cutting medium 16 will not slip or escape from the securing means 12, 14 as the edge 18 is moved through the cutting medium 16.

Alternatively, instead of an arm assembly 20, the securing means 12, 14 may be a gripper assembly 22. Generally, the gripper assembly 22, shown as the lower securing means 14 in FIGS. 1–3, includes at least one gripper 34 and at least one slide 36. The gripper 34 may be in operatively associated with (e.g., mounted on) a track or slide 36 to facilitate lateral movement of the gripper 34. In this regard, the cutting medium 16 may be angularly adjusted by laterally positioning the gripper 34 in a specific location. More specifically, in one embodiment of the present invention, the gripper 34 is operatively associated with a tubular slide 36 upon which the gripper 34 can be laterally positioned along the length of the tubular slide 36. The gripper 34 itself may be fixed in a desired position along the tubular slide 36 by a tightener 64, which may be selected from the group consisting of wing bolts, screws, pins, clamps, toggles, latches, hooks, lugs, couplings, cables or by other similar devices.

Generally, the function of the gripper 34 is to secure a portion of the cutting medium 16 to the gripper assembly 22. In this way, the gripper 34 holds the cutting medium 16 in a specific angular orientation and inhibits the cutting medium 16 from slipping or escaping from the gripper assembly 22. Preferably, the gripper 34 is selected from the group consisting of clamps, toggles, prongs, latches, rivets, pins, screws and other similar devices.

In another embodiment of the present invention, in order to accommodate varying lengths, shapes, sizes and forms of cutting mediums and to ensure that the desired angular orientation of the cutting medium is achieved, the upper and/or lower securing means 12, 14 may be vertically adjustable. For example, the arm assembly 20 may be vertically adjusted and held in place on the stand 38 by at least one tightener 64 selected from the group including bolts, clamps, pins, rivets, hooks, latches, lugs, screws and other similar devices. Similarly, the vertical position of the gripper 34 on the gripper assembly 22 may be vertically adjusted and secured by a tightener 64.

To facilitate accurate, reproducible and reliable measurements of sharpness, the cutting medium 16 can be placed under tension. In one embodiment of the present invention, the upper and lower securing means 12, 14 are capable of tensioning the cutting medium 16 along at least one longitudinal axis of the cutting medium 16. Providing longitudinal tension to the cutting medium 16 facilitates movement of the edge 18 through the cutting medium 16 by preventing creasing or bending of the cutting medium 16 as the edge 18 moves longitudinally through the cutting medium 16. Such creasing or bending of the cutting medium 16 can compress the cutting medium 16, which can affect the density of the cutting medium 16 such that false or inaccurate sharpness measurements can result. The longitudinal tension imparted by the securing means 12, 14 to the cutting medium 16 should not be so great as to tear or rip the cutting medium 16 but should nonetheless be sufficient to substantially prevent flexing of the cutting medium 16 so as to provide a relatively rigid cutting medium 16, which facilitates reliable sharpness measurements. Longitudinal tension may be provided to the cutting medium 16 by the upper and lower securing means 12, 14 along an axis substantially parallel to the edge 18. As shown in FIGS. 1–3, the arm assembly 20 and the gripper assembly 22 are both capable of holding the cutting medium 16 not only at a specific angular orientation, but also with a certain degree of longitudinal tension simply by utilizing the arm adjustment mechanism 26 and/or the vertical adjustments of the securing means 12, 14. For example, the cutting medium 16 may be longitudinally tensioned by adjusting the longitudinal arcuate position of the arms 24, 25 and/or by adjusting the vertical position of the arm assembly 20 on the stand 38.

Preferably, no lateral tension is provided to the cutting medium 16 as frictional effects of the cutting medium 16 on the edge 18 and the blade 40 are inherently an indication of knife sharpness. However, in another embodiment of the present invention, slight lateral tension may be provided to the cutting medium 16 along an axis substantially perpendicular to the edge 18, preferably, in the upper portion of the cutting medium 16, to inhibit the frictional effects of the cutting medium 16 on the knife blade 40. In this regard, such tensioning may decrease the effects of friction between the cutting medium 16 and the blade 40 and the edge 18 as the edge 18 travels through the cutting medium 16. However, to avoid tearing, it should be noted that the lateral tension imparted to the cutting medium 16 should be an amount minimally sufficient to keep the sliced sections of the cutting medium 16 from contacting one another and, more preferably, to keep the sliced sections of the cutting medium 16 from substantially contacting side surfaces of the blade 40. The lateral tension imparted to the cutting medium 16 should not, however, be so great as to tear or rip the cutting medium 16. Lateral tension may be provided to an upper portion of the cutting medium 16 along an axis substantially perpendicular to the edge 18 primarily by the upper securing means 12. In an embodiment utilizing arms 24, 25 to secure the cutting medium 16, the arms 24, 25 themselves may provide the lateral tension to an upper portion of the cutting medium 16 by slightly loading the arms 24, 25 prior to attachment to the cutting medium 16. More specifically, prior to securing the arms 24, 25 to the cutting medium 16, the arms 24, 25 of the arm assembly 20 may be flexed or bent slightly inwardly, towards one another. Once preloaded, the arms 24, 25 may be connected to the cutting medium 16 by the appropriate fasteners 28. In this regard, the cutting medium 16 may be laterally tensioned.

Alternatively, in yet another embodiment, to test the effectiveness of buffing the sides of the blade 40 to reduce blade drag, the securing means 12, 14 may be capable of keeping, by applying lateral compression, at least one of the sliced portions of the cutting medium 16 substantially in contact with the blade 40. The amount of lateral compression of the cutting medium 16 should be an amount minimally sufficient to keep at least one of the sliced sections of the cutting medium 16 in contact with the blade 40. However, the lateral tension imparted to the cutting medium 16 should not be so great as to substantially increase the density of the material of the cutting medium 16, especially in the area of the cutting medium 16 to be cut by the edge 18. Lateral compression of the cutting medium 16 may be provided by the arms 24, 25 by slightly loading the arms 24, 25 outwardly before attachment to the cutting medium 16.

Thus, it can be appreciated that the securing means 12, 14 accomplishes two tasks. The primary function of the securing means 12, 14 is to angularly adjust and maintain the cutting medium 16 in at least one of a plurality of specific angular orientations. More specifically, the angular orientation of the cutting medium 16 may be adjusted by varying the longitudinal arcuate position of arms 24, 25 and/or by the lateral positioning of the gripper 34 along the slide 36 of the gripper assembly 22. Such angular orientation adjustment of the cutting medium 16 permits quantitative sharpness measurements at specific discrete segments along substantially the entire length of the edge 18 where the projection of the cutting medium (Pcm) 16 is greater than or equal to the projection of the edge (Pe) 18. In addition, the upper and lower securing means 12, 14 can also can impart longitudinal tension to the cutting medium 16 to facilitate more accurate, reliable and reproducible sharpness measurements.

As shown in FIGS. 1–3, the holding means 42 primarily functions to securely hold an edge 18. In general, the holding means 42 is operatively associated with a stand 38 as the stand 38 provides support and stability to the present invention. In one embodiment of the present invention, the holding means 42 is also operatively associated with the measuring means 44, as will be discussed below. The holding means 42 generally functions to securely hold a knife handle 41 which is connected to a blade 40 and/or an edge 18. The holding means 42 preferably holds the blade 40 such that the edge 18 can contact the cutting medium 16. More specifically, it is preferable for the holding means 42 to hold the edge 18 such that the edge 18 is oriented substantially perpendicular to the cutting medium 16. In this regard, in one embodiment of the present invention, the edge 18 moves longitudinally through the cutting medium 16. Alternatively, the edge 18 may move laterally through the cutting medium 16 (not shown).

To produce quantitative, reliable, accurate and reproducible sharpness measurements, the holding means 42 should not allow the knife handle 41 to slip or escape from the holding means 42 while the edge 18 travels through the cutting medium 16. In this regard, the holding means 42 may include an internal sleeve, jacket or insert 43 to snugly envelop at least a portion of the knife handle 41, and/or at least one edge tightener 46, which can be selected from the group including clamps which utilize screws, pins, latches, bolts, cabling and lugs, and other similar devices to fixedly fasten or tighten the knife handle 41 within the holding means 42.

In another embodiment of the invention, the angular configuration of the edge 18 may be adjusted to a plurality of cutting angles, relative to the cutting medium 16. In this regard, an adjustable holding means provides the ability to conduct sharpness measurement tests by simulating various cutting configurations. For example, the present invention may be utilized to predict and/or determine how often specific portions of an edge will require sharpening when held at cutting angles typically encountered in the meat cutting industry. Preferably, the angle alpha (α) between the edge 18 and the cutting medium 16 is between 0–180 degrees. To provide such adjustability, the holding means 42 may itself be angularly adjustable at its attachment to the stand 38 or the edge 18 may be angularly adjustable within the holding means 42. In this regard, the holding means 42 may be fixedly attached to the stand 38 at a common cutting angle or, alternatively, adjustably attached to the stand 38 by a device selected from the group including bolts, clamps, latches, pins, couplings, lugs, pins, rivets, screws, wing nuts and other similar fasteners. In another embodiment, the edge 18 itself may be adjustable to simulate various cutting angles. In this regard, where the sharpness of an edge 18 of a knife blade 40 is being measured, the knife handle 41 may be angularly positioned within the holding means 42 by adjusting the tightener 46 on the holding means 42 to securely position and hold an edge 18 at a specific angle. Alternatively, the angular configuration of the edge 18 relative to the cutting medium 16 may be adjusted simply by changing out the insert 43 or by altering the lateral and/or longitudinal position of the cutting medium 16 by adjusting the securing means 12, 14.

As shown in FIG. 1, the moving means 48 is capable of allowing relative movement of the edge 18 relative to the cutting medium 16. In this regard, the edge 18 may be moved relative to a stationary cutting medium 16 to cut through the cutting medium 16, or alternatively, the cutting medium 16 may be moved relative to a stationary edge 18. In order to provide accurate, reliable and reproducible sharpness measurements, in a preferred embodiment, the moving means 48 moves the edge 18 through the cutting medium 16 at a substantially constant velocity or with a substantially constant force. For example, where the cutting medium is 6-ply posterboard, the moving means 48 moves the edge 18 through the cutting medium 16 at a substantially constant velocity or rate of change of position of about 1.8 to 2.2 inches/second.

Preferably, the moving means 48 is operatively associated with and interposed between the holding means 42 and the measuring means 44, as shown in FIGS. 1–3. In this regard, a moving assembly 50 can be associated with the holding means 42 through the bracket 54, which is associated with the measuring means 44, to move the edge 18 at a substantially constant velocity or with a substantially constant force through the cutting medium 16. In accordance with one aspect of the invention, the moving assembly 50 is preferably an electrical or mechanical device. More specifically, a mechanical or electrical moving assembly 50 may be associated with the measuring means 44 and holding means 42 to move the edge 18 linearly or arcuately through a cutting medium 16 at a substantially constant velocity or with a substantially constant force. In particular, as illustrated in FIG. 1, a moving assembly 50, comprising an electric acme ball screw type actuator 51 and threaded drive shaft 58, is associated with the bracket 54 and the measuring means 44, which is operatively associated with the holding means 42. In this regard, due to the lever-type mechanism of the moving assembly 50, measuring means 44 and holding means 42, the moving assembly 50 is capable of moving the edge 18 linearly, through the cutting medium 16 at a substantially constant velocity. Thus, it can be appreciated that a moving assembly 50 with an electric acme ball screw type actuator 51 and associated threaded drive shaft 58 provides sharpness measurements which would be more reliable and reproducible due the lack of variations in velocity at which the edge 18 moves through the cutting medium 16. In yet another embodiment (not shown), to move the edge 18 through the cutting medium 16 with a substantially constant force or at a substantially constant velocity, the moving means 48 may include a device selected from the group consisting of weights, pulley systems, worm gears, chains and sprockets, and linear actuators, such as electric, hydraulic, or pneumatic pistons.

In another embodiment of the present invention, illustrated in FIG. 2, the moving means 48 may be manually operated by pulling downwardly on a bracket 54. The bracket assembly 54 is connected to the measuring means 44 and operatively associated with the holding means 42 and the edge 18. The bracket 54 slidably interfaces with the stand 38. A handle 56, upon which a person can grip, allows an operator to manually move the edge 18 through the cutting medium 16 at a substantially constant velocity or with a substantially constant force.

In yet another embodiment of the present invention, the moving means 48 is operatively associated with the securing means 12, 14 (not shown). The moving means 48 may be operatively associated with the securing means 12, 14 to allow movement of the cutting medium 16 while the edge 18 remains stationary. In this embodiment, the moving means 48 may be connected or attached to the securing means 12, 14 and may include an electrical or mechanical motor to move the cutting medium 16 at a substantially constant velocity or with a substantially constant force. Alternatively, the securing means 12, 14 may be moved manually while the edge 18 remains stationary.

A measuring means 44 is also provided. Generally, the measuring means 44 is designed to quantitatively measure the sharpness of an edge 18 as a specific portion of the edge 18 or consecutive discrete segments of the edge 18 relatively move relative to the cutting medium 16. In this regard, the measuring means 44 may indicate the maximum, minimum and/or the average sharpness of the edge 18 or the actual sharpness of a specific portion of the edge 18, or sharpness at discrete segments of the edge 18 along a substantial portion or the entire length of the edge 18. Such sharpness measurements are useful in establishing a universal scale and database for various types of edges, such as knives and to predict how often an edge 18, or segments thereof, need sharpening.

In order provide quantitative, accurate, reliable and reproducible sharpness measurements, the measurement means 44 should measure either the force or, alternatively, the velocity or rate at which discrete segments of the edge 18 move through the cutting medium 16. In yet another embodiment, the measuring means 44 may measure the time required for an edge 18, moving at with a substantially constant force, to travel through a given cutting medium 16. The measuring means 44 may be operatively associated with the holding means 42, the moving means 48, the edge 18, the securing means 12, 14 or the cutting medium 16. In a preferred embodiment of the present invention, as illustrated in FIGS. 1–3, the measuring means 44 is associated with and interposed between the moving means 48 and the holding means 42. In such an embodiment, the measuring means 44 measures the force on or velocity at which the edge 18 moves through the cutting medium 16.

The measuring means 44 is operatively associated and interposed between the moving means 48 and the holding means 42 and may include a force strain gauge or dynamometer 60 from which continuous sharpness measurements can be obtained as the edge 18 moves through the cutting medium 16. The moving means 48 may interface with the measuring means 44 by mutual connection to the bracket 54. Dynamometer 60 of the measuring means 44 interfaces with the holding means 42. As shown in FIGS. 1 and 2, the dynamometer 60 measures the force translated to it by the holding means 42. Specifically, the dynamometer 60 interfaces with a portion of the holding means 42 and translates to the dynamometer 60 the force required for the edge 18 to move through the cutting medium 16. The interface between the gauge 60 and the holding means 42 comprises a ballbearing or, alternatively, a clevis type mount 45.

Sharpness of the edge 18, or discrete segments thereof, can be quantitatively measured as the edge 18 moves through the cutting medium 16. In particular, as the edge 18 travels through the cutting medium 16 at a substantially constant velocity, sharper segments of the edge 18 will require less force to cut through the cutting medium 16 than duller segments of the edge 18. More specifically, when measuring the sharpness at discrete segments of the edge 18 along a substantial length of the edge 18, sharper portions of the edge 18 will require less force to cut the cutting medium 16 while duller portions of the edge 18 will require more force to cut through the cutting medium 16. In this regard, the present invention can quantitatively measure the sharpness of the edge 18 at discrete segments along a substantial length of the edge 18 to indicate which areas of the edge 18 are sharpest or dullest and, consequently, which areas need sharpening most often. Thus, it can be appreciated that quantitative sharpness measurements of the edge 18 and/or consecutive discrete segments thereof can be quantitatively measured by a single operation of the present apparatus.

Similarly, the present invention can also quantitatively measure edge sharpness of the edge 18, a specific portion of the edge 18 or at discrete segments along a substantial length or the entire length of the edge 18, by measuring the velocity at which the edge 18 or such discrete segments thereof move through the cutting medium 16. In such an embodiment, the moving means 48 moves the edge 18 through the cutting medium 16 with a substantially constant force. In this embodiment, the measuring means 44 includes a velocity or time measuring instrument, such as a speedometer, a tachometer or a timer which is operatively associated with the moving means 48 or, alternatively, the holding means 42. More particularly, the velocity or time measuring instruments may be connected to the moving or holding means 48, 42 such that velocity or time measurements commence as a substantially constant force is applied to the edge 18 and terminate when a particular portion of the edge 18 to be measured has cut through the cutting medium 16. In this regard, where the edge 18 is moved through the cutting medium 16 with a substantially constant force, sharper segments of the edge 18 will travel through the cutting medium 16 at a higher velocity or in a lesser amount of time than duller segments of the edge 18. Thus, it can be appreciated that quantitative and consecutive measurements of sharpness of the edge 18 at specific portions along the length of the edge 18 can be provided by the present invention.

Alternatively, in other embodiments (not shown), the measuring means 44 can be operatively associated with the cutting medium 16 and the securing means 12, 14 by connecting, for example, a measuring device such as a force strain gauge, between the cutting medium 16 and at least one of the securing means 12, 14 such that the force strain gauge measures the force on the cutting medium 16 as the edge 18 moves through the cutting medium 16. In this embodiment of the present invention, the moving means 48 is operatively associated with or connected to the holding means 42 such that the measuring means 44 is not interposed therebetween. In this regard, the moving means 48, comprising a moving assembly 50, may be connected to the holding means 42 directly to move the edge 18 through the cutting medium 16. Thus, it can be appreciated that the measuring means 44 can measure the force on the cutting medium 16 as the edge 18 moves through the cutting medium 16. In yet another embodiment of the present invention, where the moving means 48 is operatively associated with the securing means 12, 14 to move the cutting medium 16 while the edge 18 remains stationary, the measuring means 44 may be operatively associated with or connected to the holding means 42 to measure the force on the edge 18 as the cutting medium 16 moves such that the edge 18 cuts the cutting medium 16.

In order to obtain accurate, reliable, and reproducible sharpness measurements, especially where the sharpness of discrete segments of the edge 18 along a substantial length of the edge 18 is being measured, the measuring means 44 may interface with a device capable of automatically determining the sharpness measurements for a specific portion or discrete segments of the edge 18. The measuring means 44 may interface with a device which is capable of receiving, processing and calculating sharpness measurements for specified discrete segments of the edge 18.

Preferably, the measuring means 44 interfaces with an analog or digital device, such as a computer (not shown), which can receive inputs from the aforementioned sharpness measuring instruments, such as the dynamometer 60, to compute sharpness measurements. In this regard, the computerized device may calculate the actual, maximum, minimum and/or average force required for a specific portion of the edge 18 to travel at a substantially constant velocity through the cutting medium 16. Alternatively, the computerized device may calculate the actual, maximum, minimum and/or the average velocity of or time in which the specific portion of the edge moving with a substantially constant force travelled through a given length of cutting medium. The computerized device would especially assist in determining the sharpness of discrete segments of an edge 18. The computerized device may receive inputs regarding the force required for consecutive discrete segments of the edge to cut through the cutting medium 16 or the velocity at which the edge 18 is moved through the cutting medium 16 in order to correlate such sharpness measurements with the specific locations of the discrete segments along the edge 18.

The present invention also provides for a method for testing the sharpness of edges. Generally, the method includes the steps of securing a cutting medium 16 at a specific angular orientation, holding an edge 18 at a specific angular orientation, contacting the edge 18 with the cutting medium 16, moving the edge 18 through the cutting medium 16 and quantitatively measuring the sharpness of the edge 18, or discrete segments thereof, along a predetermined length of the edge 18.

The step of securing a cutting medium 16 at a specific angular orientation determines the length of edge 18 to be quantitatively measured for sharpness. The method of the present invention can be used to quantitatively and consecutively measure the sharpness of discrete segments of an edge 18 along a substantial length of the edge 18, including, along the entire length of the edge 18. Assuming the edge 18 contacts the cutting medium 16 at or substantially near the upper boundary of the cutting medium 16, as shown in FIGS. 4a–c, the length of the portion of the edge 18 to be quantitatively measured for sharpness substantially corresponds to the projection of the cutting medium (generally denoted as Pcm). As shown in FIG. 4a, where the cutting medium 16 is secured by the securing means 12, 14 oriented at approximately ninety degrees, a specific portion of the edge 18 will be quantitatively measured for sharpness. The length of the specific portion of the edge 18 to be measured substantially equals the length of the cutting medium's projection, Pcm, which, in this instance, substantially corresponds to the thickness of the cutting medium 16.

Consecutively and quantitatively measuring the edge sharpness of discrete segments along a substantial length of the edge 18 can be accomplished in accordance with the features of the present invention simply by securing the cutting medium 16 at a specific angular orientation. Such sharpness measurements are especially useful in determining which sections of an edge 18 have dulled the most or remained relatively sharp after significant use. The results of such wear can be used to determine when and which sections of knives will require sharpening most often and to determine the edge materials which remain sharp for longer periods of time. Also, the present apparatus and method allow for assessment of various sharpening techniques. Where consecutive quantitative sharpness measurements are required for discrete segments along a substantial portion of an edge 18, the cutting medium 16 should be secured at a specific angular orientation such that the length of the projection of the cutting medium 16, Pcm, shown in FIG. 4b, substantially corresponds to the total length of discrete segments of the edge 18 to be measured for sharpness (assuming the edge 18 contacts the cutting medium 16 at or substantially near the upper boundary of the cutting medium 16). From the foregoing it will be seen that an average sharpness of a substantial portion of the edge 18 can be determined simply by averaging the sharpness measured at the discrete segments, or, alternatively, the dullest and/or sharpest portion of an edge may be determined.

The cutting medium 16 may also be secured at a specific angular orientation such that the sharpness of an edge can be measured consecutively and quantitatively at discrete segments of the edge 18 along the entire length of the edge. The projection of the cutting medium 16, Pcm, as shown in FIG. 4c, should be selected such that Pcm is at least substantially equal to or greater than the length of the edge 18. From the foregoing, it is readily apparent that an average sharpness of the entire edge 18 can be determined by averaging the sharpness measurements of the discrete segments of the edge 18, or alternatively, the fullest and sharpest portions of the edge 18 can be determined.

Thus it is seen that the upper and lower securing means 12, 14 can be angularly adjusted in order to obtain sharpness measurements along the desired length, or portions thereof, of the edge 18. In this regard, arm assemblies 20 and gripper assemblies 22 may be adjusted, as previously described, to adjust and position the cutting medium 16 to a desired location and/or angular orientation. Once positioned, the securing means 12, 14 may be fastened or fixed in the desired location by appropriate devices to affix the cutting medium 16 in the desired angular orientation.

In addition to securing the cutting medium 16 in a specific angular orientation, the cutting medium 16 may be tensioned by at least one of the securing means 12, 14 to provide for an accurate measurement of sharpness of the edge 18. In a preferred embodiment method of the present invention, the cutting medium 16 is not laterally tensioned as the frictional effects of the cutting medium 16 on the edge 18 and the blade 40 are inherently indicators of sharpness. Nonetheless, the cutting medium 16 may be laterally tensioned by at least one of the securing means 12, 14. The amount of lateral tension of the cutting medium 16 should be selected so as to be sufficient to keep the sliced sections of the cutting medium 16 from contacting one another, and preferably, from substantially contacting the blade 40. Tensioning the cutting medium 16 along a longitudinal axis of the cutting medium 16 facilitates movement of the edge 18 through the cutting medium 16 by inhibiting the effects of creasing or bending of the cutting medium 16. The amount of longitudinal tension should be selected so as to substantially provide for a relatively rigid cutting medium 16.

Another important aspect of the present invention includes the step of securing the edge 18 at a predetermined angular configuration. In this regard, the predetermined angular configuration may be selected and maintained by the holding means 42 as the edge 18 cuts through the cutting medium 16 to simulate various cutting configurations used by medical and/or food industry fabricators. Typically, as shown in FIGS. 4a–4c, the edge 18 may be selected to cut through the cutting medium 16 at an angle alpha ($\alpha$). Angle alpha ($\alpha$) may measure between 0–180 degrees, depending upon the orientation of the cutting medium 16. Thus, it can be appreciated that the present invention may assist in determining or predicting, for selected edge angular configurations and materials, which areas of an edge 18 need sharpening most often and whether an edge remains sharp for longer periods of time for different edge angular configurations. In turn, such predictability may enhance production and reduce the stress and strain on personnel who cut various food products.

Once the cutting medium 16 has been secured at a specific angular orientation and the angular configuration of the edge 18 has been secured, the edge 18 may contact the cutting medium 16. The edge 18 may contact the cutting medium 16 by adjusting the position of the holding means 42 or, alternatively, by adjusting the vertical positioning of the cutting medium 16 by adjusting the upper and/or lower securing means 12, 14. More particularly, in accordance with the present invention, before the test commences, a portion of the edge 18 located at a specific location along the length of the edge 18 may contact the notched area of the cutting medium 16, depending upon whether a specific portion or discrete segments along a substantial or the entire length of the edge 18 is to be measured. As shown in FIG. 4a, where a specific portion of an edge 18 is to be measured, such specific portion of the edge 18 should substantially contact a notched area of the cutting medium 16, generally located within the interior of the cutting medium 16 and not within the boundary region of the cutting medium 16. Alternatively, as shown in FIG. 4b, where discrete segments along a substantial length of the edge 18 are to be measured, the edge 18 should contact the upper portion of the cutting medium 16 at one of the two outer limits of the length of the edge 18 to be measured, depending upon the angular orientation of the cutting medium 16. Where discrete segments along the entire length of the edge 18 are to be measured consecutively, as shown in FIG. 4c, one of the two ends of the edge 18 should contact the upper portion of the cutting medium 16, depending upon the angular orientation of the cutting medium.

The present method also includes the step of moving the edge 18 through the cutting medium 16. In order to accurately measure the sharpness of an edge 18, in one embodiment of the invention, the edge 18 or a knife can be initially moved through the edge or boundary of the cutting medium 16 before the test commences. Initially notching or cutting through the boundary of the cutting medium 16 may improve the accuracy of edge sharpness measurements because the surface tension or hardness in the area of the boundary may differ slightly or even substantially from the hardness or density of the remaining portion of the cutting medium 16. As can be appreciated, the length of such a notch substantially depends upon the material characteristics of the cutting medium 16, especially in the boundary regions of the cutting medium 16. With regard to a cutting medium 16 composed of 6-ply posterboard, the notch is at least 0.1 inches in length and preferably at least 0.25 inches in length.

Once in contact with the cutting medium 16, the edge 18 may relatively move relative to the cutting medium 16 at a substantially constant rate. Alternatively, the edge 18 may relatively move relative to the cutting medium 16 with a substantially constant force. Moving the edge 18 through the cutting medium 16 may be accomplished by imparting a force to the holding means 42 through the measuring means 44 which is operatively associated with the holding means 42. The edge 18 may be moved through said cutting medium 16 by applying a force, either manually or motorized, to the holding means 42 to move the holding means 42, and thereby the edge 18, either linearly or arcuately, through the cutting medium 16. In another embodiment, a force may be applied, manually or motorized, to the measuring means 44, which is operatively associated with the holding means 42, to move the edge 18 through the cutting medium 16. In a preferred embodiment, where the cutting medium 16 is composed of 6-ply posterboard, the edge 18 moves through a cutting medium at a substantially constant velocity, ranging from about 1.8 to about 2.2 inches/second. Alternatively, the cutting medium 16 may be moved while the edge 18 remains stationary where the moving means 48 is operatively associated with the securing means 12, 14.

Generally, as an edge 18 moves through a cutting medium 16, sharper portions of the edge 18 will move through the cutting medium 16 more easily than duller portions of the edge 18. For purposes of consistency, comparability and reproducibility, an empirical database can be established using the present invention so that edge 18 performance can be accurately predicted by quantitative measurements. Sharpness measurements may be determined simply by observing the displayed force, velocity or time indicators from the abovenoted measuring instruments. For example, in a preferred embodiment, the force required for a specific portion or discrete segments along a substantial length of the edge 18 can be determined by viewing the measurements shown on a force strain gauge or dynamometer 60. More specifically, where the sharpness of discrete segments along an edge 18 is to be determined, sharpness measurements displayed on the dynamometer 60 may be observed as discrete segments of the edge 18 cut through the cutting medium 16 at a substantially constant velocity. In this regard, quantitative and consecutive sharpness measurements of discrete segments of an edge 18 along a substantial or the entire length of the edge 18 may be obtained by observing and correlating the force measurements to the specific discrete segments of the edge 18. The measuring step may further include the step of calculating the sharpness of the edge 18 in relation to specific discrete segments of the edge 18. For purposes of accuracy, precision and reproducibility, calculating and correlating the sharpness measurements from the measuring means 44 with the corresponding discrete segments of an edge 18 along a substantial or entire length of the edge 18 would be especially beneficial. Specifically, the sharpness measurements may be inputted into a computer capable of correlating such measurements with the specific locations of the discrete segments along the edge 18.

The present invention may also be used in connection with testing a number of physical properties of various materials. More specifically, the present invention may be used for determining, among other things, material properties such as the shear stress, resistance to shear forces, notch sensitivity, tearing properties, longitudinal frictional coefficients, travel velocities through the material, abrasiveness, longitudinal material lattice compositions, hardness and toughness of materials and/or whether a material is of a uniform density. In this regard, the apparatus and associated method could form the basis of establishing material test standards as governed by the American National Standards Institute and/or the American Society of Testing Materials.

Generally, in order to obtain such measurements, the present invention may be first used to quantitatively measure the sharpness of cutting edges, specifically, knife blades. Once determined, the cutting edge may or may not be sharpened and again tested for sharpness. In this regard, a database may be developed based upon the rates of dulling and quantitative measurements of sharpness of newly "sharpened" cutting edges. Such a database may be developed for specific cutting edges and/or cutting edges of various shapes and materials. In view of their known quantitative sharpness and the associated rate of dulling through various materials, the sharpened cutting edges may then be used according to the present invention to measure the shear stress, hardness, toughness or the uniformity of density of various materials simply by moving the sharpened cutting edge through the material to be tested at a substantially constant velocity or with a substantially constant force. For example, variations in the amount of force or velocity at which the "sharpened" cutting edge moves through the material may indicate non-uniformity of composition or variations in the density of the material. Such measurements may then be compared with the known, expected or calibrated physical properties of the material. Thus, it can be appreciated that the present invention may be used in connection with examining the physical properties of a variety of materials, such as meat, wood, fabric, cardboard, paper, paperboard, rubber, plastic and other synthetic and/or organic materials.

The foregoing description of the invention has been presented for purposes of illustration and description. Further, the description is not intended to limit the invention to the form disclosed herein. Consequently, variations and modifications commensurate with the above teachings, and the skill or knowledge in the relevant art are within the scope of the present invention. The preferred embodiment described herein above is further intended to explain the best mode known of practicing the invention in various embodiments and with various modifications required by their particular applications or uses of the invention. It is intended that the appended claims be construed to include alternate embodiments to the extent permitted by the prior art.

What is claimed is:

1. An apparatus for measuring the sharpness along a predetermined length of an edge, comprising:

means for securing a cutting medium, wherein said securing means allows for adjustment of said cutting medium to a plurality of specific angular orientations;

means for holding an edge so that said edge may contact said cutting medium, said edge being an edge of a knife blade projecting from a handle;

means for relatively moving said edge at a substantially constant velocity relative to said cutting medium; and means for quantitatively measuring the force required to relatively move said edge relative to said cutting medium.

2. An apparatus as claimed in claim 1,
wherein said securing means is operatively associated with said moving means to move said cutting medium.

3. An apparatus as claimed in claim 1,
wherein said securing means allows for tensioning said cutting medium.

4. An apparatus as claimed in claim 1,
wherein said securing means allows for fixedly maintaining said cutting medium in at least one of said plurality of specific angular orientations.

5. An apparatus as claimed in claim 1,
wherein said holding means allows for angular adjustment of said edge in a plane perpendicular to said cutting medium to simulate various cutting angles.

6. An apparatus as claimed in claim 1,
wherein said holding means allows for fixedly keeping said edge in at least one of said various cutting angles.

7. An apparatus as claimed in claim 1,
wherein said moving means is operatively associated with said measuring means.

8. An apparatus as claimed in claim 1,
wherein said measuring means is operatively associated with said holding means.

9. An apparatus as claimed in claim 1,
wherein said measuring means is operatively associated with said securing means.

10. An apparatus as claimed in claim 1,
wherein said securing means allows for adjusting and fixedly maintaining said cutting medium in at least one of said plurality of specific angular orientations to permit quantitative measurement of the sharpness of discrete segments of said edge along substantially the entire length of said edge.

11. An apparatus for measuring the sharpness along a predetermined length of a knife edge, comprising:

gripper assemblies for securing a cutting medium, wherein said gripper assemblies include means which allow for adjustment of said cutting medium to a plurality of specific angular orientation;

a knife handle holder capable of holding a knife handle so that the knife edge is at a desired angle with respect to said cutting medium;

a moving assembly operatively associated with the knife holding means that can move the knife edge at a substantially constant velocity relative to said cutting medium; and a force strain gauge operatively associated and interposed between the moving assembly and said knife holder capable of measuring the force required to relatively move said knife edge relative to said cutting medium.

* * * * *